(12) United States Patent
Parten et al.

(10) Patent No.: US 6,384,268 B1
(45) Date of Patent: May 7, 2002

(54) TREATMENT OF FORMALDEHYDE-CONTAINING MIXTURES

(75) Inventors: William David Parten, North Yorkshire; Stephen Patrick Harrison, Cleveland; John Stuart Martin, Cheshire, all of (GB)

(73) Assignee: Ineos Acrylics UK Limited, Hampshire (GB)

( * ) Notice: Subject to any disclaimer, the term of this patent is extended or adjusted under 35 U.S.C. 154(b) by 0 days.

(21) Appl. No.: 09/481,564

(22) Filed: Jan. 11, 2000

Related U.S. Application Data

(63) Continuation of application No. PCT/GB98/02026, filed on Jul. 10, 1998.

(30) Foreign Application Priority Data

Jul. 11, 1997 (GB) .............................................. 9714540

(51) Int. Cl.[7] .............................................. C07C 67/48
(52) U.S. Cl. ...................................................... 560/218
(58) Field of Search .......................................... 560/218

(56) References Cited

U.S. PATENT DOCUMENTS 3,440,276 A    4/1969   Wolf et al.

FOREIGN PATENT DOCUMENTS

GB            1107234         3/1968

Primary Examiner—Paul J. Killos
(74) Attorney, Agent, or Firm—Pillsbury Winthrop LLP

(57) ABSTRACT

A process for the removal of formaldehyde species from a liquid carboxylic acid or carboxylic acid ester stream which forms a two-phase mixture with water is disclosed which comprises the step of subjecting the liquid organic mixture to at least one liquid liquid extraction stage wherein water is used as an extractant to produce an organic phase stream which is substantially formaldehyde free and an aqueous phase stream which contains substantially all of the formaldehyde in the output streams from the liquid liquid extraction. The process is particularly useful for reducing the formaldehyde content of a methyl methacrylate product stream.

14 Claims, 1 Drawing Sheet

U.S. Patent

TREATMENT OF FORMALDEHYDE-CONTAINING MIXTURES

Figure 1:
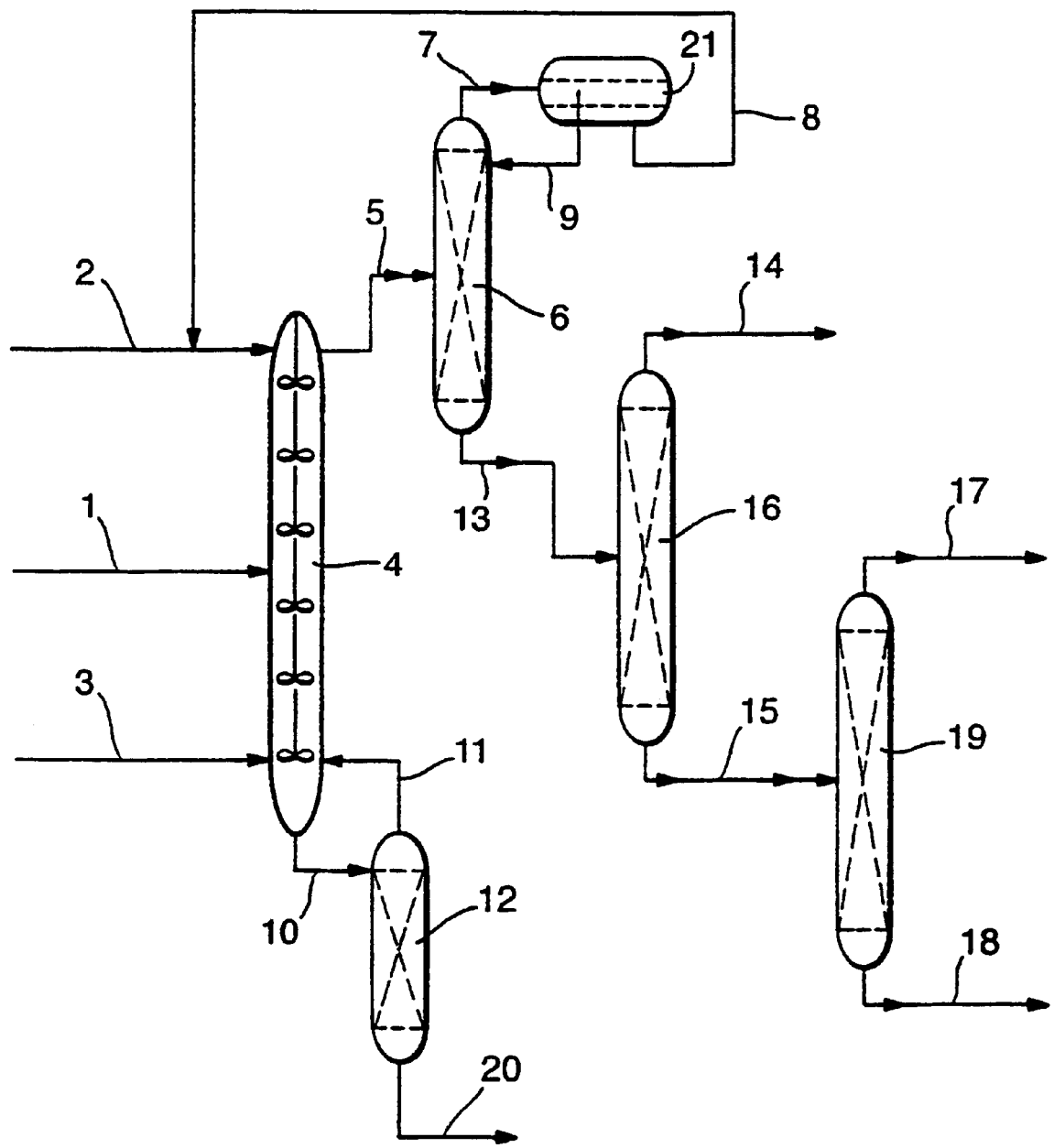

This is a Continuation of: International Appln. No. PCT/GB98/02026 filed Jul. 10, 1998 which designated the U.S.

The present invention relates to a process for the treatment of formaldehyde-containing mixtures, especially for the treatment of methyl methacrylate streams which contain formaldehyde.

Conventionally, methyl methacrylate has been produced industrially via the so-called acetone-cyanohydrin route. The process is capital intensive and produces methyl methacrylate at a relatively high cost.

Other processes for the production of methyl methacrylate are disclosed in U.S. Pat. No. 3535371, U.S. Pat. No. 4,336,403, GB-A-1 107234 , JP-A-63002951 which require the condensation of propionic acid with formaldehyde or methylal in the presence of methanol. These references do not, however, describe how the methyl methacrylate product may be separated and recovered from the residual formaldehyde and other components which may be found in the reactor product stream.

It has now been found that the residual formaldehyde can be separated from a methyl methacrylate stream in a manner which may also allow the recycling of the formaldehyde to the initial condensation process. Although the invention has been found to be particularly useful for the separation of formaldehyde from a methyl methacrylate-containing stream, it will be understood that the process may also be applied to the removal of formaldehyde species from a variety of other organic mixtures.

Accordingly the present invention provides a process for the removal of formaldehyde species from a liquid organic mixture comprising at least a carboxylic acid or carboxylic acid ester and formaldehyde species and which forms a two-phase mixture with water, which comprises the step of subjecting the liquid organic mixture to at least one liquid liquid extraction stage wherein water is used as an extractant to produce an organic phase stream and an aqueous phase stream such that the organic phase stream contains a significantly reduced concentration of formaldehyde species compared to the liquid organic mixture.

By formaldehyde species we mean that the formaldehyde in the liquid stream is normally present in the form of adducts with water or polar organic compounds such as alcohols. Normally free formaldehyde is in the form of a light gas and would not therefore form part of the liquid mixture. References to formaldehyde are therefore taken to include formaldehyde species which are adducts of formaldehyde with components of the liquid mixture or with water.

Water is used to extract formaldehyde from the liquid stream, but this need not be pure water. The water used may contain small amounts of dissolved compounds which do not significantly affect the extraction of formaldehyde species into the aqueous phase. In operating a manufacturing process which incorporates the formaldehyde removal process of the invention, it may be convenient and economical to use an aqueous stream from another part of the process as the water extractant of the present process. The suitability of any particular aqueous stream for use as an extractant may be readily determined by analysis or experiment. Preferably the content of such an aqueous stream is known and comprises compounds which are present in the organic stream or which can be readily removed from the organic stream. Thus water as used in this specification should be taken to include such an aqueous stream which may contain a low level of dissolved compounds, e.g. traces of organic materials.

The concentration of formaldehyde in the organic phase stream output from the liquid extraction process is preferably <10%, more preferably <5%, and especially <1% of the concentration of formaldehyde in the untreated formaldehyde-containing mixture. The concentration of formaldehyde in the organic output will be largely determined by the equipment and method used, e.g. the number of stages, level of mixing or separation achieved, etc. A final concentration of much less than 1% of the starting concentration may be achievable by suitable processing.

The liquid organic mixture is subjected to at least one liquid-liquid extraction stage. Preferably more than one liquid-liquid extraction stage is performed, for example between one and twenty, preferably between one and ten liquid-liquid extraction stages may be performed, although the number of stages required will depend upon the nature and relative proportions of the compounds in the mixture. When we refer to separation stages, we mean theoretical stages. Certain process equipment, e.g. a rotating disc contactor column presents a continuum of one phase so that defined physical stages may not be evident although the theoretical stages present may be calculated.

Although the aqueous phase from the at least one liquid-liquid extraction stage may be disposed of, preferably the aqueous phase is subjected to a further at least one liquid-liquid extraction stage wherein it is mixed with a suitable organic liquid to extract (strip) from the aqueous stream organic compounds other than formaldehyde. Suitable liquids include non-polar organic solvents which are immiscible with water such as alkanes, e.g. petrol, hexane or heptane, other higher alkanes or ethers, or other organics. Preferably the liquid liquid extraction stage comprises a counter-current process in which an organic stream is run as a counter current to the water so that the extraction of formaldehyde into the aqueous phase and stripping of organics from the aqueous phase into the organic solvent may be accomplished in a single operation. Using this arrangement the formaldehyde-containing mixture is fed between the water feed and the organic stream, preferably approximately centrally between the two feeds which comprise the counter-current flow. The preferred counter-current flow can conveniently be established in well-known liquid-liquid extraction apparatus such as a rotating disk contactor or a cascade of mixer-settlers.

As discussed above the process of treatment according to the invention has been found to be particularly useful to remove formaldehyde from a formaldehyde-containing liquid organic mixture which is a product of a process for the production of an alkyl ester of an acrylic acid (e.g. methyl methacrylate) in which an alkyl ester of an alkanoic acid is reacted with methanol and formaldehyde in the presence of a catalyst. In particular, one useful application of the invention has been found to be the removal of formaldehyde from a methyl methacrylate containing stream in which formaldehyde is present, for example as produced by a process for the production of methyl methacrylate from the condensation reactions of methyl propionate with formaldehyde and methanol over a suitable catalyst.

Therefore, according to a further aspect of the invention, we provide a process for the production of methyl methacrylate comprising the steps of:

(i) reacting propionic acid or an ester thereof with formaldehyde or a precursor thereto in a condensation reaction stage to produce a gaseous product stream comprising methyl methacrylate, residual formaldehyde, residual propionic acid or an ester thereof and by-products;

(ii) liquefying at least a portion of the gaseous product stream to form a liquid product stream containing substantially all of the methyl methacrylate, the residual formaldehyde, the by-products and the remainder of the residual propionic acid or an ester thereof;

(iii) subjecting the liquid product stream to at least one liquid liquid extraction stage wherein water is used as an extractant to produce an organic phase stream which is substantially formaldehyde free and an aqueous phase stream which contains substantially all of the residual formaldehyde.

Preferably the methyl methacrylate is produced by the condensation of methyl propionate with formaldehyde or a precursor thereto, e.g. methylal, and particularly by the condensation of methyl propionate with formaldehyde. By-products from the reaction include water, diethyl ketone (DEK), propionic acid (PA), methacrylic acid (MAA) and methyl isobutyrate (MIB). The reaction is preferably carried out in the presence of methanol. Methanol may also be produced in the reactor as a product of side reactions, for example the reaction of methyl esters of propionic acid and methacrylic acid with water in the feed. Therefore the gaseous product stream is also likely to contain methanol.

The condensation reaction is preferably conducted in the presence of a catalyst. Suitable catalysts include alkali metals and alkaline earth metals, optionally supported on a suitable support, e.g. a caesium catalyst on a silica support.

The condensation reaction stage may be conducted at any suitable temperature and pressure. Typically, the condensation reaction stage is conducted at a temperature from 250 to 400° C. and preferably from 300 to 375° C. Typically, the condensation reaction stage is conducted at a pressure from $10^4$ to $10^6$ N.m$^{-2}$ and preferably from $10^5$ to $10^6$ N.m$^{-2}$.

The gaseous product stream is liquefied, for example by quenching, condensing or by other means known to those skilled in the art of such processes, such that the gaseous product stream is cooled to the extent that the methyl methacrylate is liquefied and withdrawn as a liquid product stream. It is most likely that this stream will not be pure and that other components in reactor product stream will also be present in this liquid product stream. In addition to by-products, the liquid stream is likely to contain residual reactants, i.e. methyl propionate, methanol and formaldehyde. Especially it is likely that as formaldehyde cools it will react to form adducts with water and methanol and that these adducts will be present with the MMA in the liquid product stream. It may be possible to arrange the quench or condenser such that it produces several streams of differing composition besides the liquid product stream containing the MMA. These other streams may be recycled to the condensation reactor, further processed or disposed of as effluent as appropriate The liquid-liquid extraction stage is preferably carried out in an apparatus in which a counter-current flow of water and an organic liquid is established to avoid loss of organic components other than formaldehyde in the aqueous extract. Although the organic liquids mentioned previously may be used, a preferred organic liquid for this purpose is methyl propionate which is already present in the process and which can be reused in the methyl-methacrylate manufacturing process.

The aqueous stream will emerge from the extractor saturated with organics and the organic stream will emerge saturated with water and so preferably both streams are distilled to remove organics and water respectively which can be referred to the extractor. After distillation the aqueous stream may be disposed of as an effluent but it can contain a significant amount of formaldehyde adducts and so it may be preferable to further process this stream and recycle the formaldehyde to the condensation reaction stage.

We have found that the partition of formaldehyde between the organic and aqueous phases is enhanced if the concentration of methanol in the liquid stream to be separated is relatively low. That is to say, a low level of methanol in the liquid product stream favours the movement of formaldehyde into the aqueous phase, i.e. the partition coefficient of formaldehyde (defined as the ratio of the concentration of formaldehyde in the organic phase to the concentration of formaldehyde in the aqueous phase) is relatively low. Preferably the concentration of methanol in the liquid product stream is less than 5% by weight more preferably less than 2.5%, especially less than 1% by weight. At least some of the excess methanol in the liquid product stream, if any, is therefore preferably removed, e.g. by distillation or by varying the conditions under which the gaseous reactor product stream is liquefied or by other means, before the liquid-liquid extraction treatment. The excess methanol may be conveniently removed with some of the excess methyl propionate by distilling off an azeotropic mixture of methyl propionate and methanol and returning it to the reactor.

The invention is illustrated, by way of example only, in FIG. 1 which shows a flowsheet for the separation of methyl methacrylate from formaldehyde and other compounds using liquid-liquid extraction.

In FIG. 1, the gaseous stream from a reactor (not shown) in which methyl methacrylate (MMA) is produced from the condensation reaction between methyl propionate (MeP), methanol and formaldehyde, is quenched to form a liquid product stream (1) containing MMA, formaldehyde, methanol, MeP, water, methyl isobutyrate (MIB), propionic acid (PA), methacrylic acid (MAA) and diethyl ketone (DEK) which is passed to a liquid-liquid extractor (4) and to which is also fed a water stream (2) and a MeP stream (3). The liquid-liquid extractor separates the incoming streams into an organic stream (5) and an aqueous stream (10). The organic stream (5) contains the bulk of the MeP, MMA, PA, MIB, and DEK fed to the extractor and contains an equilibrium quantity of water. The aqueous stream (10) contains the bulk of the water and formaldehyde (in the form of adducts with water and methanol) and also contains an equilibrium quantity of less polar molecules, mainly MeP. In this system, methanol divides between the organic and aqueous stream and is likely to be more soluble in the aqueous phase than the organic phase.

The organic stream (5) is passed to a distillation column (6) for removal of water. The top product from (6) condenses to form two liquid phases which are split in a decanter (21). The aqueous layer (8) is recycled to the top of the extractor and the organic layer (9) is refluxed back to (6). The bottom stream from (6) is passed to the distillation column (16) where MeP is taken as the overhead product (14). A proportion of this stream may be recycled back to the extractor and used as the organic feed (3) and the rest may be re-fed to the condensation reactor.

The bottom product from distillation column (16) is fed to distillation column (19). Stream (17) is the top product from (19) and contains MMA and components which boil close to MMA such as DEK and MIB. This product may be further purified by, for example, distillation to increase the purity of the MMA. The bottom product from (19) is stream (18) which contains molecules heavier than MMA, for example PA and M1. These may be re-fed to the condensation reactor.

The aqueous stream (10) is fed to the top of a distillation column (12) and acts as the reflux on that column. Stream

(11) is the condensed overhead product from (12) and is fed to the bottom of the extractor (4). The bottom product from (12) contains water and formaldehyde adducts and may either be disposed of or further processed to remove water so that the formaldehyde adducts can be recycled to the condensation reactor.

The invention is further illustrated by reference to the following examples.

EXAMPLE 1

A stock solution containing the following components was prepared:- formaldehyde 13.4 wt %, methanol 19.56 wt %, methyl propionate 28.42 wt %, methyl methacrylate 18.33 wt %, water 20.29 wt %. 100 ml of the stock solution was mixed with 100 ml of demineralised water. The resulting mixture was then allowed to phase separate into a first organic and a first aqueous phase. A portion of the first organic phase was recovered and a further extraction performed with an equal volume of demineralised water to form a second organic and a second aqueous phase. Likewise, a portion of the first aqueous phase was recovered and a further extraction was performed with stock solution to form a third organic and a third aqueous phase. The composition of the organic and aqueous phases was determined and are presented in Table 1.

TABLE 1

|  | First Organic Phase | First Aqueous Phase | Second Organic Phase | Second Aqueous Phase | Third Organic Phase | Third Aqueous Phase |
| --- | --- | --- | --- | --- | --- | --- |
| Volume % of Extraction | 21.3 | 78.7 | 45 | 55 | 23.9 | 76.1 |
| Composition of Phase w/w % | | | | | | |
| Formaldehyde | 2.3 | 7.8 | 0.4 | 0.3 | 4.4 | 11.5 |
| Methanol | 3 | 11.6 | 0.6 | 2.1 | 6.3 | 17.8 |
| Methyl Propionate | 48.8 | 4.8 | 49.8 | 3 | 45.5 | 7.4 |
| MMA | 36.8 | 1.3 | 39.9 | 0.8 | 32.6 | 2.6 |
| Water | 9.1 | 74.4 | 9.4 | 93.8 | 11.2 | 60.6 |

EXAMPLE 2

Three stock solutions of methyl methacrylate containing formaldehyde, methanol, methyl propionate, water and other impurities were made up to compositions containing approximately 15%, 7.5% and 2% w/w of methanol. The compositions are given in Table 2. The level of methyl propionate was adjusted as the methanol level was changed to simulate removal of methyl propionate with the methanol as an azeotropic mixture.

TABLE 2

| Components | Solution A (wt %) | Solution B (wt %) | Solution C (wt %) |
| --- | --- | --- | --- |
| HCHO | 7.12 | 4.3 | 3.31 |
| Methanol | 1.9 | 7.4 | 14.9 |
| Methyl propionate | 35.7 | 44.9 | 52.8 |
| Methyl isobutyrate | 0.04 | 0.04 | 0.03 |
| MMA | 32 | 25.6 | 15.6 |
| Propionic acid | 4.39 | 3.51 | 2.15 |
| Methacrylic acid | 0.19 | 0.14 | 0.08 |
| Water | 18.6 | 14.1 | 11.1 |

TABLE 3

| Components | Solution A (wt %) | Solution B (wt %) | Solution C (wt %) |
| --- | --- | --- | --- |
| HCHO | 7.12 | 4.3 | 3.31 |
| Methanol | 1.9 | 7.4 | 14.9 |
| Methyl propionate | 35.7 | 44.9 | 52.8 |
| Methyl isobutyrate | 0.04 | 0.04 | 0.03 |
| MMA | 32 | 25.6 | 15.6 |
| Propionic acid | 4.39 | 3.51 | 2.15 |
| Methacrylic acid | 0.19 | 0.14 | 0.08 |
| Water | 18.6 | 14.1 | 11.1 |

The feed mixtures were washed in water using a single-stage mixer -settler unit at three different feed: wash water ratios. The results are shown in Table 3. The results show that as the proportion of methanol in the feed mixture is reduced, the partition coefficient of formaldehyde between the organic and aqueous phases (defined as the ratio of the concentration of formaldehyde in the organic phase to the concentration of formaldehyde in the aqueous phase) decreases such that more formaldehyde enters the aqueous phase as the methanol concentration is reduced. By contrast the partition of methyl methacrylate into the organic phase increases at low methanol concentrations thus the separation of methyl methacrylate from formaldehyde is greatly improved at relatively low concentrations of methanol.

EXAMPLE 3

A five stage mixer-settler solvent extraction unit was set up by half-filling the cells with the heavy phase, followed by topping up with the light phase until the cells just overflow. The light and heavy phase pumps were switched on followed by the mixer-settler stirrers/impellers. The flow rates of each phase were equal and set to achieve a 60 minute residence time across the whole mixer settler. In this experiment the heavy phase was water, fed into cell 1, and the light phase was methyl propionate, fed into cell 5. The mixer-settler was allowed to equilibrate for approximately 60 minutes.

An aqueous solution of 4.4 wt % propionic acid was prepared from propionic acid and water, and the accurate level was determined by titration with 0.0095N NaOH (aq). A solution of 4% w/w formaldehyde in methyl propionate was prepared by extracting 35 wt % formalin solution into methyl propionate. When the mixer-settler was stable, the distilled water feed to the mixer-settler was exchanged for the propionic acid solution, and the methyl propionate feed to the mixer settler was exchanged for the methyl propionate containing formaldehyde. Final samples of the aqueous output from cell 5 and of the methyl propionate output from cell 1 were analysed for formaldehyde by titration using sodium sulphite as described in "Formaldehyde" by J. F. Walker (Reinhold/Chapman & Hall 1964—ACS monograph series 159) and for propionic acid by NaOH titration. The results in wt % are given in Table 4.

TABLE 4

|  | Propionic acid | | Formaldehyde | |
| --- | --- | --- | --- | --- |
|  | Cell 5 | Cell 1 | Cell 5 | Cell 1 |
| Aqueous Layer | 0.04% | 2.02% | 5.42% | 0.01%* |
| Organic Layer | 0.02% | 4.18% | 0.69% | 0.01%* |
| Cell Partition Coefficient | 0.5 | 2.07 | 0.127 | 1* |

TABLE 4-continued

|  | Propionic acid | | Formaldehyde | |
|---|---|---|---|---|
|  | Cell 5 | Cell 1 | Cell 5 | Cell 1 |
| Overall MS Partition Coefficient | 104.5 | | 0.00185 | |

Results marked * indicate that the limit of detection of formaldehyde by the titration method used was 0.01%. The results demonstrate that formaldehyde may be extracted from an organic stream into water without the loss of organic acid in the water phase.

EXAMPLE 4

The mixer settler extraction unit used in Example 3 was set up with methyl propionate and water counter-current flow as described in Example 3, each fed at a rate of 3 ml/minute and allowed to settle to a steady state. An organics mixture containing the components listed in Table 5, was prepared and fed to stage 3 of the mixer settler at a rate of 6 ml/minute. Samples were taken from cells 1 and 5 and analysed by gas chromatography. The formaldehyde concentration was determined also by sulphite titration, as described in Example 3. The results are given in Table 5. The result given for formaldehyde is that found by titration. The results show that the formaldehyde from a mixed organics stream may be extracted into an aqueous stream without significant loss of the other organic components from the organic mixture.

TABLE 5

|  | Wt % in mixture | Wt % in aqueous output | Wt % in organic output |
|---|---|---|---|
| Methyl Propionate | 65 | 7.82 | 68.3 |
| Methyl methacrylate | 15 | 0 | 10.67 |
| Diethyl ketone | 5 | 0 | 3.45 |
| Methacrylic acid | 5 | 0.01 | 3.28 |
| Propionic acid | 5 | 0.03 | 2.92 |
| formaldehyde | 2 | 3.06 | 0.18 |
| water | 2.5 | 90.6 | 10.87 |
| methanol | 0.5 | 0.44 | 0.32 |

What is claimed is:

1. A process for the removal of formaldehyde species from a liquid organic mixture comprising at least a carboxylic acid or carboxylic acid ester and formaldehyde species and which forms a two-phase mixture with water, which comprises the step of subjecting the liquid organic mixture to at least one liquid liquid extraction stage wherein water is used as an extractant to produce an organic phase stream and an aqueous phase stream such that the organic phase stream contains a significantly reduced concentration of formaldehyde species compared to the liquid organic mixture.

2. A process as claimed in claim 1 wherein said organic phase stream contains less than 2.5% by weight of formaldehyde.

3. A process as claimed in claim 2 wherein the concentration of formaldehyde in said organic phase stream is less than 10% of the concentration of formaldehyde in said liquid organic mixture.

4. A process as claimed in claim 3 wherein said organic phase stream contains less than 0.5% by weight of formaldehyde.

5. A process as claimed in claim 1, wherein between one and twenty successive liquid-liquid extraction stages are performed.

6. A process as claimed in claim 1, further comprising a step in which said aqueous phase stream is contacted with an organic solvent which forms a separate phase on admixture to water.

7. A process as claimed in claim 6, wherein the liquid liquid extraction stage comprises a counter-current process wherein a stream of said organic solvent is run as a counter current to the water and the liquid carboxylic acid or carboxylic acid ester stream is fed into the process at a stage between the organic solvent stream feed and the aqueous stream feed.

8. A process as claimed in either claim 6 or claim 7, wherein said organic solvent comprises methyl propionate.

9. A process as claimed in claim 1, wherein said liquid carboxylic acid or carboxylic acid ester stream comprises methanol and at least some of the methanol is removed from the liquid product stream before it is subjected to a liquid-liquid extraction process.

10. A process as claimed in claim 1 wherein said liquid carboxylic acid or carboxylic acid ester stream contains at least 5% w/w of methyl methacrylate.

11. A process as claimed in claim 1 wherein said liquid carboxylic acid or carboxylic acid ester stream comprises at least 20% methyl propionate.

12. A process as claimed in claim 1 wherein said formaldehyde-containing liquid carboxylic acid or carboxylic acid ester stream is a product of a process for the production of an alkyl ester of an acrylic acid in which an alkyl ester of an alkanoic acid is reacted with methanol and formaldehyde in the presence of a catalyst.

13. A process as claimed in claim 12, wherein said formaldehyde-containing liquid carboxylic acid or carboxylic acid ester stream is a product of a process for the production of methyl methacrylate by the reaction of methyl propionate with formaldehyde and methanol in the presence of a catalyst.

14. A process for the production of methyl methacrylate, which process comprises the steps of (i) reacting propionic acid or an ester thereof with formaldehyde or a precursor thereto in a condensation reaction stage to produce a gaseous product stream comprising methyl methacrylate, residual formaldehyde, residual propionic acid or an ester thereof and by-products;

(ii) liquefying at least a portion of the gaseous product stream to form a liquid product stream containing substantially all of the methyl methacrylate, the residual formaldehyde, the by-products and the remainder of the residual propionic acid or an ester thereof;

(iii) subjecting the liquid product stream to at least one liquid liquid extraction stage wherein water is used as an extractant to produce an organic phase stream which is substantially formaldehyde free and an aqueous phase stream which contains substantially all of the residual formaldehyde.

* * * * *